United States Patent [19]

Blank et al.

[11] Patent Number: 4,881,560
[45] Date of Patent: Nov. 21, 1989

[54] DISPENSER FOR DENTAL FLOSS

[76] Inventors: Eric Blank, 81 New Bridge Rd., Sudbury, Mass. 01776; Robert A. Endelson, 330 E. 79th St., New York, N.Y. 10021

[21] Appl. No.: 204,491

[22] Filed: Jun. 9, 1988

[51] Int. Cl.⁴ .............................................. A61C 15/00
[52] U.S. Cl. .................................... 132/324; 206/63.5
[58] Field of Search ............... 132/321, 322, 323, 324, 132/325, 326, 327, 328, 329; 206/63.5

[56] References Cited

U.S. PATENT DOCUMENTS

| | | | |
|---|---|---|---|
| 2,083,398 | 6/1937 | Rohland | 206/388 |
| 2,929,541 | 3/1960 | Castelli et al. | 132/321 |
| 3,918,466 | 11/1975 | Peebles, Jr. | 132/323 |
| 3,930,059 | 12/1975 | Wells | 427/2 |
| 4,141,519 | 2/1979 | Tarrson et al. | 132/321 |
| 4,162,688 | 7/1979 | Tarrson et al. | 132/322 |
| 4,211,330 | 7/1980 | Strock | 206/581 |
| 4,327,755 | 5/1982 | Endelson | 132/324 |

Primary Examiner—Gene Mancene
Assistant Examiner—Adriene J. Lepiane
Attorney, Agent, or Firm—Hamilton, Brook, Smith & Reynolds

[57] ABSTRACT

A flat, dental floss dispenser in a credit card format having a flat coil of floss in a well within the dispenser. A cutting blade is formed as a tab projecting from a plate which is supported on a step projecting from the well bottom inside a peripheral edge. Wall members project from the well bottom and surround at least a portion of the plate. The blade is a substantially U-shaped tab raised from the plate and forms two spaced acute angular intersections at its line of intersection with the plate, one being larger than the other. The larger functions to cut the floss, and the smaller to retain the cut end on the dispenser. The supply coil has a wrapping to assist in maintaining its integrity during manufacturing and in the dispensing process and the floss is withdrawn through the center of the coil.

13 Claims, 2 Drawing Sheets

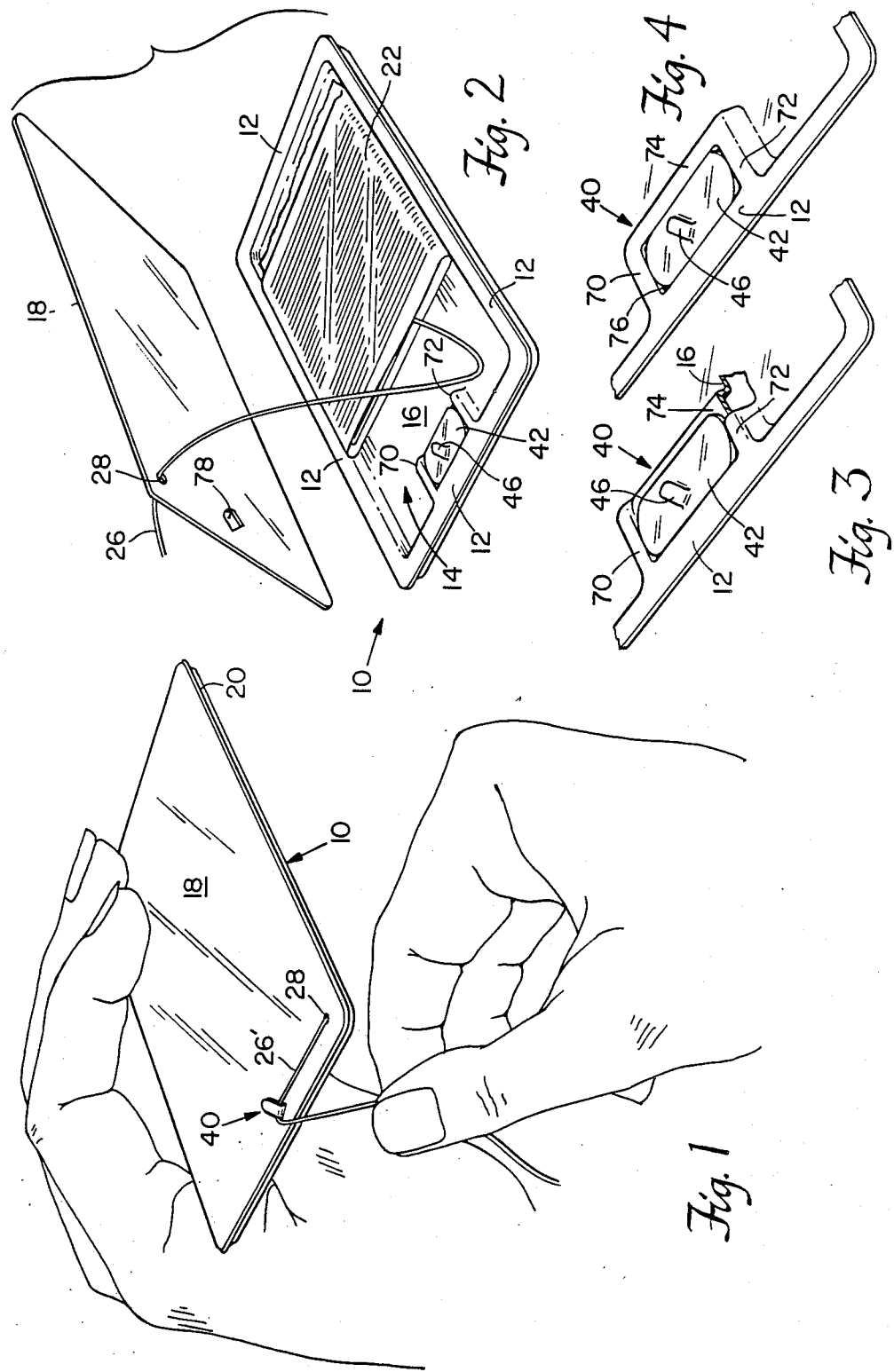

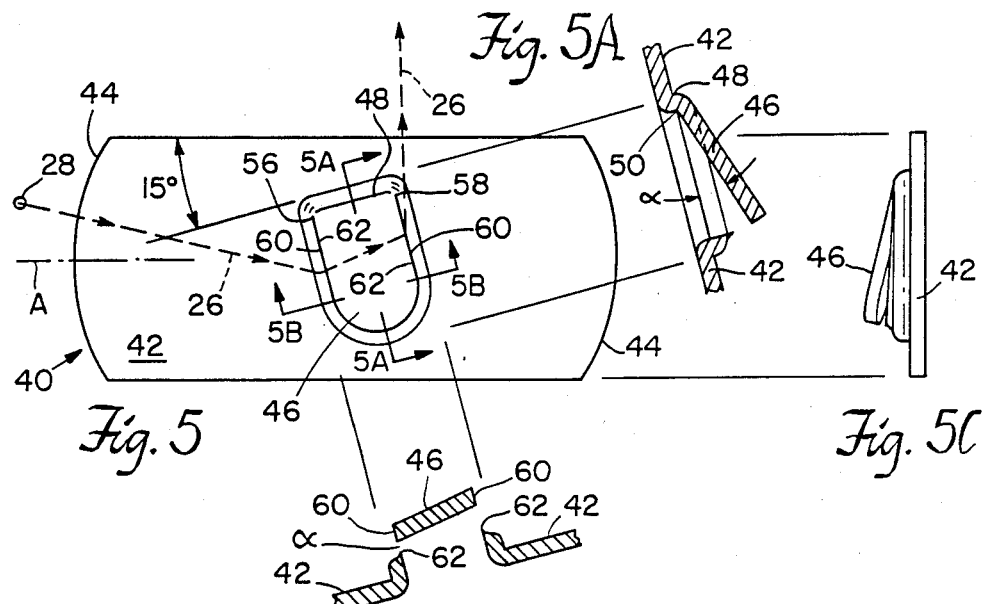
Fig. 5  Fig. 5A  Fig. 5C
Fig. 5B
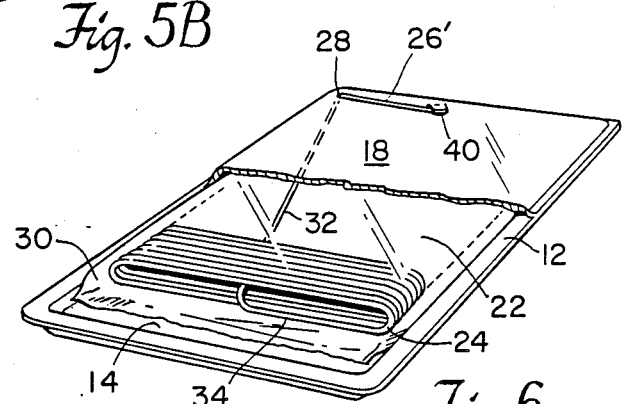
Fig. 6
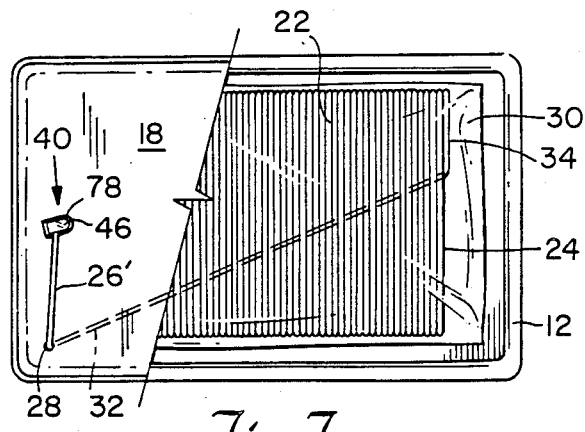
Fig. 7

DISPENSER FOR DENTAL FLOSS

FIELD OF THE INVENTION

This invention relates to dental floss dispensers in general and more particularly to a thin, flat, dental floss dispenser in a credit card format.

BACKGROUND OF THE INVENTION

U.S. Pat. No. 4,327,755, which issued on May 4, 1982, to Robert A. Endelson, one of the present inventors, discloses a thin, flat, dental floss dispenser in a credit card format which permits the dispenser to be conveniently carried in a wallet, shirt pocket, purse or the like. The dispenser included a base panel in which there is a shallow well defined by a peripheral ridge. A supply of dental floss in flatened form is located in the well with its leading end passing out of an aperture in a face panel which is secured to the ridge which defines the well.

The floss is severed by a blade which is located in an edge notch formed in the base panel. The blade may assume a number of forms, one being a lug pressed up from a plate located in a rectangular edge notch, and the other being a conventional blade exposed by a triangular edge notch. The presence of either edge notch presents problems in sealing the face panel to the base.

One of the objects of the present invention is to provide a dispenser in a credit card format retaining all of the advantages of the prior dispenser but which is easier to manufacture.

Another object of this invention is to provide a new cutting blade assembly and means for securing it within the dispenser.

Still another object of the present invention is to provide better means for storing the floss within the dispenser and for withdrawing the floss from the supply.

SUMMARY OF THE INVENTION

The invention is embodied in a thin dental floss dispenser in a credit card format as is the dispenser disclosed in U.S. Pat. No. 4,327,755. The dispenser includes a base panel which has a peripheral ridge thereby defining a shallow well having a substantially flat bottom. A flattened supply coil of dental floss is located in the well and covered by a matching face panel which is marginally bonded to the ridge. The face panel has an aperture to permit the leading end of the coil to be pulled out of the well. A blade for cutting the floss is made in the form of a tab which projects from a plate. The plate may be positioned on a locating step which projects upwardly from the well bottom and supports the plate with the blade extending through an aperture in the face panel.

Wall members may be formed in the well bottom which surround at least a portion of the plate in a location inwardly of the ridge. The wall members may engage either two or three sides of the plate as it rests upon the step with the inner edge of the ridge engaging the remaining side of the plate. The presence of the step and/or the wall members leaves the entire surface of the ridge available for bonding to the face panel of the dispenser.

The cutting blade is a substantially U-shaped tab raised from the plate, forming two acute angular intersections at its line of intersection with the plate. The angular intersection of the tab and the plate which is closer to the aperture from which leading into the floss projects, is the smaller of the two angles and is formed to hold the floss after a piece is cut. The second angular intersection between the tab and the plate is larger and is formed to sever the floss.

The leading edge of the coil is drawn from the end of the coil remote from the aperture and passes through the center of the coil which assists in maintaining the integrity of the coil as the floss is drawn from it.

The actual flattened coil may be provided with a wrapping to assist in maintaining its integrity during manufacturing and in the dispensing process. It may also be positioned in the dispenser in unsupported fashion.

The above and other features of the invention including various and novel details of construction and combinations of parts will now be more particularly described with reference to the accompanying drawings and pointed out in the claims. It will be understood that the particular dispenser for dental floss embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 1 is a perspective view of a dental floss dispenser in a credit card format made in accordance with the present invention.

FIG. 2 is an exploded perspective view of the dispenser.

FIG. 3 is a perspective view of one means for locating the cutting knife in the dispenser.

FIG. 4 is a view similar to FIG. 3 showing an alternative embodiment of the locating means.

FIG. 5 is a plan view on an enlarged scale of the cutting and holding blade.

FIG. 5A is a sectional view taken on the line 5A—5A of FIG. 5.

FIG. 5B is a sectional view taken on the line 5B—5B on FIG. 5.

FIG. 5C is an end view of the cutting and holding blade.

FIG. 6 is a perspective view of the dispenser with part of the face panel removed to expose the supply coil of floss, and FIG. 7 is a perspective view thereof.

DETAILED DESCRIPTION OF THE INVENTION

Referring to FIGS. 1 and 2, there will be seen a dental floss dispenser made in accordance with the present invention in credit card format. It includes a base panel 10 with a peripheral ridge 12 which defines a shallow well 14 having a substantially flat bottom 16.

A matching face panel 18 is marginally bonded, as for example, at 20 in FIG. 1, to the peripheral ridge 12 around the entire periphery of the panel 10.

The panels 10 and 18 of the dispenser are preferably made of a flexible, synthetic, plastic material such as polyvinylchloride or other thermoplastic material. Commensurate with credit card dimensions, the dispenser is approximately a three inch by two inch rectangle with slightly rounded corners.

A supply of dental floss generally indicated 22 is located in the well 14. The floss supply is in the form of a flatened helical coil 24. The leading end 26 (FIG. 2) of the floss extends through the center of the helical coil 24 and extends out of the opposite end. When the floss is pulled out of the dispenser, through an aperture 28 in the face panel 18, it is being drawn from the opposite end of the coil, i.e., the end remote from the aperture 28. This assists in maintaining the integrity of the coil when floss is drawn from it. The coil is positioned in the well 14 initially with the leading end remote from the aperture 28. It is then threaded through the center of the coil and out through the aperture in the assembly process.

As best seen in FIGS. 6 and 7, the floss supply 22 comprising the helical coil 24 is contained within a thin, light wrapping in the form of a plastic pouch 30 which in turn may be secured by adhesive or other equivalent means to the bottom 16 of the well 14. The purpose of the pouch 30 is to help maintain the integrity of the coil when the floss is being pulled from it and during the assembly process. Any equivalent securing means may be employed or, as taught in the earlier Endelson patent, the integrity of the coil may be contained by setting the wax constituent of the floss.

Also as seen in FIGS. 6 and 7, the leading end of the floss extends out of the aperture 28 with the next contiguous portion 32 located within the coil 24 and thence coming from the helix 34 which is most remote from the aperture 28.

The dispenser includes a blade generally indicated 40 for cutting and holding the floss. As best seen in FIGS. 5 through 5C on enlarged scale, the blade 40 includes a substantially rectangular plate 42 having, if desired, curved ends 44. The cutting blade, per se, is a tab 46 pressed out of the plate 42. At the line of intersection 48 between the tab 46 and the plate 42, there are two acute angular intersections 56 and 58. The angular intersections are formed by the edge 60 of the tab portion 46 and the corresponding edge 62 of the plate from which the tab was pressed.

As best seen in FIG. 5B, the tab portion 46 is inclined at an acute angle with the plane of the plate 42 resulting in the angular intersections being of unequal size. The smaller angle α is closer to the aperture 28 than the larger angle at the opposite side of the tab.

Note also in FIG. 5 that the tab axis is inclined at an acute angle, herein illustrated as 15°, from the major axis A of the plate 42.

Again with reference to FIG. 5, in operation, the leading end 26 of the floss which extends out of the aperture 28, is engaged in the angle α between the edges 60 and 62 of the tab and the plate, passed under the tab 46 and engaged in the opposite acute angle whereupon it is cut. The larger angle effects the cutting and the smaller angle 60 then retaining the cut piece of floss substantially as shown in FIG. 7.

To remove another piece of floss, that portion of the floss designated 26' is removed from beneath the tab 46, an additional length of floss is pulled from the aperture 28 and again the floss is reengaged with the tab to sever a desired length with the new portion 26' remaining engaged beneath the tab after the cut piece is removed.

As seen in FIGS. 2, 3 and 4, the plate 42 is retained inwardly of the ridge 12 by a pair of wall members 72. The plate also may rest on or be secured to a step 74 (FIG. 3) which is raised from or projects above the flat bottom 16 of the well 14. The wall members 72 surround the plate 42 on two sides (FIG. 3) and the ridge 12 engages the plate on one side. If desired, an additional wall portion 14 (FIG. 4) may be formed in the base panel 10 to engage the plate 42 on the remaining side.

While the plate mounting the cutter tab 46 may be held on the step 74 by adhesive means, the wall members 70 may include grooves or gibs 76 (FIG. 4) or other equivalent holding means. This locates the cutter positively, inwardly of the ridge 12 with the tab 46 may projecting out of an opening 78 in the face panel 18 (FIG. 2) and also as seen in FIG. 1.

The wall members 70 and 72 may be located any place along the inner edge of the well 14 while maintaining a desired relationship with the aperture 28. It will be noted that the entire surface of the ridge 12 is uninterrupted and available for bonding to the mating face of the face panel 18. This assists in the ease of manufacturing and permits the interior of the dispenser to be effectively sealed except for a very small area between the tab 46 and the aperture 78 in the face panel.

We claim:

1. A thin dental floss dispenser in a credit card format, said dispenser comprising:
    a base panel provided with a peripheral ridge to define a shallow well with a substantially flat bottom,
    a flattened supply coil of dental floss located in the well,
    a matching face panel marginally bonded to the ridge,
    means to permit the leading end of the coil to be pulled out of the well,
    a blade with which to sever the floss,
    the blade being formed as a tab projecting from a plate located in the well inwardly of the ridge,
    a step projecting from the well bottom supporting the plate with the blade extending through the face panel.

2. A dispenser according to claim 1 wherein the leading end of the coil is drawn from the end of the coil remote from the blade.

3. A dispenser according to claim 1 wherein the leading end of the coil is drawn through the center of the flattened supply coil.

4. A dispenser according to claim 1 wherein the flattened supply coil is provided with a wrapping to assist in maintaining its integrity during manufacture and in the dispensing process.

5. A thin dental floss dispenser in a credit card format, said dispenser comprising:
    a base panel provided with a peripheral ridge to define a shallow well with a substantially flat bottom,
    a flattened supply coil of dental floss located in the well,
    a matching face panel marginally bonded to the ridge,
    means to permit the leading end of the coil to be pulled out of the well,
    a blade with which to sever the floss,
    the blade being formed as a tab projecting from a plate,
    wall members projecting from the well bottom and surrounding at least a portion of the plate to locate the blade inwardly of the peripheral ridge with the tab projecting through the face panel.

6. A dispenser according to claim 5 wherein the leading end of the coil is drawn from the end of the coil remote from the blade.

7. A dispenser according to claim 5 wherein the leading end of the coil is drawn through the center of the flattened supply coil.

8. A dispenser according to claim 5 wherein the flattened supply coil is provided with a wrapping to assist in maintaining its integrity during manufacture and in the dispensing process.

9. A dispenser according to claim 5 wherein the wall members engage the plate on three sides and the ridge engages the plate on one side.

10. A thin dental floss dispenser in a credit card format, said dispenser comprising:
   a base panel provided with a peripheral ridge to define a shallow well with a substantially flat bottom,
   a flattened supply coil of dental floss located in the well,
   a matching face panel marginally bonded to the ridge,
   means to permit the leading end of the coil to be pulled out of the well,
   a blade projecting through the face panel with which to sever the floss,
   said blade being a substantially U-shaped tab raised from a plate and forming two spaced acute unequal angular intersections at its line of intersection with the plate,
   the angular intersection of the tab and plate which is closer to the means to permit the leading end of the coil to be pulled out the well, being the smaller angle and formed to hold the floss after a piece is cut and the second angular intersection being larger and formed to sever the floss.

11. A dispenser according to claim 10 wherein the leading end of the coil is drawn from the end of the coil remote from the blade.

12. A dispenser according to claim 10 wherein the leading end of the coil is drawn through the center of the flattened supply coil.

13. A dispenser according to claim 10 wherein the flattened supply coil is provided with a wrapping to assist in maintaining its integrity during manufacture and in the dispensing process.

* * * * *